Briefly reviewing operation of the invention, it will be readily apparent that provision may be made for locating support carriages 18 at a number of stations along each side of the facility 10. For this purpose, it is contemplated that pairs of the brackets 36 and lower yokes 44 may be provided at frequent intervals along the structural beams 21 wherever it is anticipated that a heat exchanger might be required. When it then becomes necessary to install an exchanger at a particular location, if not already in position a support carriage 18 is installed by inserting a pin 38 through the brackets 36 and hinge arms 37 and connecting the strut 40 to the lower and upper yokes 44 and 47. The exchanger is then inserted by resting its forward end upon the shelf 48 and pushing it forwardly between the pairs of rollers 29 and 30. When inserted to the desired position, the clamps 32 are tightened to securely hold it in place. The turnbuckle 40 may also be manipulated to level the exchanger or tilt it upwardly or downwardly, as shown in the broken line positions of FIG. 3, to vary the heat exchange pattern with the ribbon 17. When a heat exchanger is no longer required at a particular location, it is removed by the reverse procedure. The support carriage 18 may be completely removed, or it may simply be pivoted downwardly to an out-of-the-way storage position as illustrated in FIG. 5 by removing the pin 46, or the pins 43 and 46, from the strut assembly.

Of course, when a heat exchanger 16 is inserted from one side of the tank structure 11, a corresponding exchanger will generally also be inserted from the opposite side as illustrated in FIG. 1 to create balanced temperature conditions across the metal bath 12 and ribbon 17. Where a generally uniform heat exchange pattern across the ribbon is sought, the opposed exchangers are longitudinally aligned in an end abutting relationship as illustrated by the pair on the right in FIG. 1. The ends of the exchangers generally extend perpendicular to the longitudinal axis as illustrated in the embodiment at the left in FIG. 1. In order to avoid creation of an abrupt temperature differential at the point where the two ends abut, which might result in a longitudinal streak in the ribbon 17, the ends may be arranged diagonally as illustrated by the aligned pair in FIG. 1 so that the line along which they abut is not parallel to the direction of advance of the ribbon. Should additional heat exchange capacity be desired in the central region, the exchangers may be offset and overlapped as illustrated by the pair on the left in FIG. 1. To that end, a third bracket 36 may be provided with the previously described pair at the heat exchanger stations along at least one side of the tank structure 11, as shown in FIG. 1, so that the support carriages 18 can be offset to carry the opposed exchangers in overlapping, parallel relationship.

It is to be understood that the forms of the invention herewith shown and described are to be taken as preferred embodiments of the same, and that various changes in the shape, size and arrangement of parts may be resorted to without departing from the spirit of the invention.

I claim:

1. In apparatus for the manufacture of flat glass by the float process including a bath of molten metal continued within an elongated tank structure having opposite sides, and a heat exchanger extending transversely above the ribbon of glass as it advances across the molten metal bath between said opposite sides, the improvement comprising a support carriage affixed to the tank structure along the side thereof through which said heat exchanger extends, said support carriage including inner and outer pairs of spaced, vertically aligned, rotatable rollers located closely adjacent said side, the rollers of each said pair being spaced apart a distance slightly greater than the depth of said heat exchanger so that their peripheral surfaces engage the top and bottom surfaces of said heat exchanger whereby said exchanger is contilevered over said ribbon.

2. Apparatus for the manufacture of flat glass by the float process as claimed in claim 1, wherein said support carriage includes a pair of end plates, said rollers engaging said heat exchanger extending between said end plates.

3. Apparatus for the manufacture of flat glass by the float process as claimed in claim 2, wherein said rollers engaging said heat exchanger are freely rotatable with their axles carried by said end plates, whereby said heat exchanger can be moved longitudinally through said support carriage.

4. Apparatus for the manufacture of flat glass by the float process as claimed in claim 1, including means pivotally connecting said support carriage to said tank structure at its inner end and a strut supporting the outer end of said carriage.

5. Apparatus for the manufacture of flat glass by the float process as claimed in claim 4, wherein said strut is adjustable in length whereby said support carriage and heat exchanger can be pivoted vertically about said pivotal connection.

6. Apparatus for the manufacture of flat glass by the float process as climed in claim 2, claim 3 or claim 4, including a shelf at the outer end of said support carriage for carrying the end of said heat exchanger as it is being inserted into or removed from said support carriage.

7. Apparatus for the manufacture of flat glass by the float process as claimed in claim 2, claim 3 or claim 4, including clamp means on said end plates for selectively engaging the side walls of said heat exchanger to immobilize said exchanger within said support carriage.

8. In apparatus for the manufacture of flat glass by the float process including a bath of molten metal contained within an elongated tank structure having opposite sides, and a heat exchanger extending transversely above the ribbon of glass as it advances across the molten metal bath between said opposite sides, the improvement comprising a support carriage affixed to the tank structure along the side thereof through which said heat exchanger extends, said support carriage comprising means engaging the top and bottom surfaces of said heat exchanger whereby said exchanger is cantilevered over said ribbon, and including a pair of end plates secured in spaced parallel relation, spaced pairs of inner and outer freely rotatable rollers having their axles carried by said end plates with their peripheral surfaces comprising said surface engaging means, a hinge arm extending from the inner end of each said end plate, a spaced pair of brackets secured to the structural framework of the tank structure, a pin extending through said hinge arms and brackets to hingedly secure said support carriage to said tank structure, and a removable strut extending between the outer end of said support carriage and said structural framework for maintaining said carriage and heat exchanger in operative position.

\* \* \* \* \*

USE OF SUBSTITUTED-3-PHENACYLIDENEPHTHALIDES AS CORN PLANT GROWTH REGULANTS

This invention relates to regulating the growth of corn plants utilizing substituted-3-phenacylidene-phthalides. More particularly, the method of the present invention is concerned with a method of treating a corn plant with a substituted-3-phenacylidenephthalide or composition containing such a compound in order to effectively alter the development of the reproductive components of the corn plant.

The use of 3-phenacylidenephthalide to inhibit root geotropism of cress and ryegrass seedlings has been described by Brown et al in *Pesticide Science*, Vol. 4, (1973) pg. 473–484 and in *Experimentia*, Vol. 28, (1972) pg. 1290–1291.

U.S. Pat. No. 4,129,729 discloses 3-phenacylidenephthalimidines and their naphthoyl derivatives of the formula

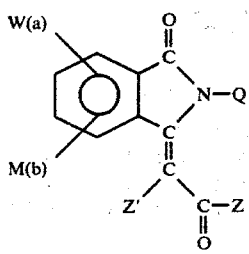

wherein Z is phenyl, naphthyl, biphenylyl or substituted phenyl, there being from 1 to 5 substituents selected from alkyl of 1 to 3 carbon atoms, alkoxy of 1 to 4 carbon atoms, halogen, nitro and trifluoromethyl, Z' is hydrogen or bromine, W is halogen, M is hydroxy, alkoxy of 1 to 4 carbon atoms, nitro or amino, a is 0 to 4, b is 0 to 2, the sum of a+b is 0 to 4, Q is hydrogen, alkyl of 1 to 3 carbon atoms, phenyl, halophenyl, nitrophenyl, trifluoromethylphenyl, tolyl, anisyl or tosylamino, and Z is hydrogen or OH; which display biological activity when used in the treatment of plants.

In accordance with the novel aspects of the present invention, the development of male reproductive components of a corn plant is altered by applying to said corn plant before or during the early stages of reproductive differentiation an effective, non-lethal amount of a 3-phenacylidenephthalide of the formula

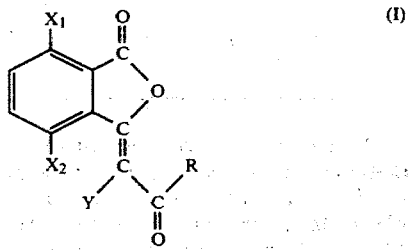

wherein R is selected from the group consisting of naphthyl, phenyl and substituted phenyl containing from 1 to 5 substituents selected from the class consisting of lower alkyl, lower alkoxy, halogen, trifluoromethyl and nitro; $X_1$ and $X_2$ are independently selected from the group consisting of hydrogen, halogen and lower alkoxy; and Y is selected from the group consisting of hydrogen, chlorine and bromine; provided that R is not 4-nitrophenyl and further provided that when $X_1$ is lower alkoxy, R is not 2,5-dimethoxyphenyl.

It is preferred that the substituted phenyl radicals represented by R contain one or two substituents selected from the group consisting of lower alkoxy, halogen and nitro. Also it is preferred that $X_2$ is hydrogen.

It will be recognized that 3-phenacylidenephthalides of formula (I) of this invention contains a carbon-to-carbon double bond with two different groups or atoms attached to each carbon. Such compounds may thus exist in the form of cis and trans geometric isomers, and both of said isomers, along with mixtures thereof, are contemplated within the scope of this invention.

The terms "lower alkyl" and "lower alkoxy" as employed herein designates alkyl and alkoxy radicals having from one to four carbon atoms inclusive. Groups representative of these alkyl and alkoxy radicals include, for example, methyl, ethyl, propyl, isopropyl, butyl, t-butyl, methoxy, ethoxy, propoxy, isopropoxy, butoxy, t-butoxy and the like.

The term "halogen" as used herein includes chloro, bromo, fluoro and iodo.

Illustrative of the substituted phenyl radicals represented by R are mono-substituted phenyl wherein the substituent is in the ortho, meta or para position, for example, methoxyphenyl, butoxyphenyl, chlorophenyl, bromophenyl, fluorophenyl, iodophenyl, nitrophenyl, trifluoromethylphenyl, ethylphenyl, butylphenyl, and the like, and the di-, tri-, tetra- and penta-substituted phenyl groups wherein the substituents are the same or different and are located in the 2, 3, 4, 5 or 6 positions of the phenyl ring, for example, dichlorophenyl, dimethoxyphenyl, (methoxy) (chloro)phenyl, (butoxy)-(nitro)-phenyl, dimethylphenyl, tribromophenyl, trimethoxyphenyl, tetrafluorophenyl, (methoxy) (tetrafluoro)-phenyl and the like.

The compounds represented by formula (I) above have been found to be effective in altering the development of the reproductive components of corn plants. As used herein, the alteration of the "development of the reproductive component" of the corn plant is understood to mean the modification of the normal sequential development of said component to maturity. Such modifications are most readily observed as inhibition of tassel growth, inhibition of lateral tassel branches, flowering inhibition, etc. The compounds of formula (I) have been particularly effective in altering the male reproductive component, namely the tassel.

The invention contemplates the alteration of the development of the reproductive components of healthy corn plants by applying an effective, non-lethal amount of a 3-phenacylidenephthalide of formula (I) to said corn plant before or during the early stages of the development of said reproductive component referred to herein as reproductive differentiation. As a result of such application, tassel size can be reduced or eliminated, thus reducing or eliminating the labor required by hybrid seed corn producers to manually detassel said corn plants.

As used herein, the term "active ingredient" refers to the 3-phenacylidenephthalides of formula (I).

In accordance with the novel aspects of the present invention, the 3-phenacylidenephthalides of formula (I) were tested in accordance with the following procedures:

ple, male reproductive differentiation of Gaspe corn begins during kernel formation while reproductive differentiation of A-619 corn begins within the first 8 to 12 days after seedling emergence. The determination of when reproductive differentiation occurs is within the skill of the art. By way of example and for purposes of illustration only, the preferred application time for most varieties used in the Midwest section of the United States ranges from 3 to 25 days after seedling emergence. Varieties used in foreign countries may require applications ranging from 1 to 40 days from seedling emergence.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention generally contain from about 5 to 95 parts active ingredient, about 1 to 50 parts surface-active agent and about 4 to 94 parts solvents, all parts being by weight based on the total weight of the composition.

In selecting the appropriate rate of application of the active ingredient, it will be recognized that precise rates will also be dependent upon the mode of application, plant variety, soil conditions and various other factors known to those skilled in the art. While a rate of about 0.056 to 5.6 kilos per hectare is preferred, higher rates of up to 56 kilos per hectare may be used, depending upon the factors noted above.

This invention, however, does not comtemplate the use of phytotoxic rates which exert a herbicidal effect.

In addition, it will be recognized that single or multiple applications may be used to exert the desired response.

It has been reported in *Pesticide Science*, Volume 4, pages 473–484 (1973), that compounds utilized in the method of the present invention may be prepared under anhydrous conditions by treating a solution of phthalic or substituted phthalic anhydride in boiling toluene with phenacylidenetriphenylphosphorane. A similar Wittig type reaction is described in *Tetrahedron Letters*, No. 28, pages 2357–2360 (1965), for the preparation of 3-phenacylidenephthalide. This latter publication indicates that the reaction proceeds readily in the absence of a solvent. These reactions, however, present a number of problems including poor separation of isomeric reaction products, limited availability of the phosphorane starting material, relatively low yields and the like.

Harris et al in *Aust. J. Chem.*, 1977, 30, pg. 2231 and 2238 describe the preparation of phenacylidenephthalide by dehydrobromination of the -brominated phenacylphthalide.

It has been found that 3-phenacylidenephthalides of formula (I) can be conveniently prepared in relatively high yields, and can be easily isolated from the reaction mixtures, by a similar dehydrohalogenation process. In such a process the starting materials are 3-($\alpha,\alpha$-halophenacyl) or 3-($\alpha,\alpha$-dihalophenacyl) phthalides in an inert organic liquid medium, and a tertiary aliphatic or heterocyclic amine is employed to serve as a scavenger or acceptor for the released hydrogen halide. The starting phthalides can be readily obtained by halogenation of a 3-phenacylphthalide with one or two equivalents of chlorine or bromine. A great number of the unhalogenated 3-phenacylphthalides are described in U.S. Pat. No. 3,407,206. The halogenation and subsequent dehydrohalogenation can, if desired, be carried out sequentially in a single reaction vessel without the need for isolation of the intermediate halogenated phenacylphthalide.

The dehydrohalogenation reaction is facilitated by first dissolving or suspending the halogenated 3-phenacylphthalide in an inert organic solvent. Suitable solvents for this purpose include ethyl acetate, the alkylene halides such as chloroform, carbon tetrachloride, methylene chloride, ethylene dichloride, etc., and the lower boiling aliphatic hydrocarbons such as the pentanes, hexanes, heptanes and octanes. To the solution or suspension, there is added a tertiary amine base in an amount which is at least equimolar to the amount of the $\alpha$-halogenated phenacylphthalide. Preferably said base is employed in a slight excess such as about 1.1 mole of base per mole of $\alpha$-halogenated phenacylphthalide. Suitable bases for use herein include the aliphatics such as trimethylamine, triethylamine, triisopropylamine and N-butyl dimethylamine, the aliphatic-aromatics such as dimethyl or diethylaniline, and the heterocyclics such as pyridine or the picolines.

The dehydrohalogenation reaction can be conducted wholly at room temperature within a few hours. Moderate heating to about 100° C. can be employed, but temperatures below about 60° C. are preferred to avoid enhancement of excessive by-product formation. The reaction proceeds readily at atmospheric pressure, and agitation of the reaction mixture is desirable but not essential. Upon completion of the reaction, the recovery and purification of the phenacylidenephthalide product can be effected by washing with dilute aqueous hydrochloric acid to remove unreacted base. After drying, the product can be recrystallized from ethanol or a mixture thereof with chloroform or dimethylformamide.

The following illustrative, non-limiting examples will serve to further demonstrate to those skilled in the art the manner in which specific compounds within the scope of this invention can be prepared. In the examples, all parts are parts by weight unless otherwise expressly stated.

EXAMPLE 4

Preparation of 3-(4'-methoxyphenacylidene)phthalide.

To a solution of 27.6 gm (98 mmol) of 3-(4'-methoxyphenacyl)phthalide in 80 ml of glacial acetic acid at room temperature, 16 gm (0.1 mol) of bromine in 100 ml of acetic acid was added with stirring over a 15 minute period with decolorization taking place. The resulting solution was stirred an additional 5 minutes and was then poured slowly with strong agitation into 250 ml of iced water. Solid sodium sulfite was added in small portions until the initial yellow color of the solution was discharged. The solid, 3-($\alpha$-bromo-4'-methoxyphenacyl)phthalide, was separated, air dried and dissolved in 300 ml of methylene chloride. This solution was then added over a 1 hour period to 50 ml of triethylamine in 100 ml of methylene chloride. After standing overnight, the organic phase was washed twice with 100 ml of 3 N HCl and concentrated. Recrystallization from 90% aqueous ethanol yielded 8 gm (29%) of a yellow solid identified as the cis isomer of 3-(4'-methoxyphenacylidene)phthalide, mp 170° C. (insoluble in hot ethanol) and 12 gm (44%) of a pink solid identified as the trans isomer, mp 145° C. (soluble in hot ethanol).

Analysis for $C_{17}H_{12}O_4$: Calculated: C=72.85; H=4.32 Found (cis): C=72.58; H=4.33 Found (trans): C=72.62; H=4.35

EXAMPLE 5

Preparation of 3-phenacylidenephthalide.

A solution of 28.5 gm (86 mmol) of 3-($\alpha$-bromophenacyl)phthalide in 150 ml of methylene chloride was added with stirring over a 1 hour period to 20 ml of triethylamine in 60 ml of methylene chloride. The slurry was stirred overnight, washed three times with dilute HCl and dried over magnesium sulfate. Evaporation of the solvent yielded 22 gm (100%) of a yellow solid. Recrystallization from ethanol, followed by washing with chloroform and filtration of insoluble material gave the cis isomer of 3-phenacylidenephthalide, mp 154° C. (insoluble in chloroform) and the trans isomer, mp 105° C. (soluble in chloroform).

Analysis for $C_{16}H_{10}O_3$: Calculated: C=76.79; H=4.07; Found (cis): C=76.40; H=4.10; Found (trans): C=76.64; H=4.07.

EXAMPLE 6

Preparation of 3-(4'-chlorophenacylidene)phthalide.

A solution of 36.5 gm (0.1 mol) of 3-($\alpha$-bromo-4'-chlorophenacyl)phthalide in 150 ml of methylene chloride was added with stirring over a 1 hour period to 15 ml of triethylamine in 150 ml of methylene chloride. The slurry was stirred overnight, washed twice with 3 N aqueous hydrochloric acid and dried over magnesium sulfate. Evaporation of the solvent yielded 18.5 gm of a yellow solid. The solid was refluxed in chloroform to give the cis isomer of 3-(4'-chlorophenacylidene)phthalide (26%), mp 204° C. (insoluble in chloroform) and the trans isomer (39%), mp 158°–159° C. (soluble in chloroform).

Analysis for $C_{16}H_9ClO_3$: Calculated: C=67.50; H=3.19; Found (cis): C=67.39; H=3.22; Found (trans): C=67.36; H=3.22.

EXAMPLE 7

In a 500 ml erlenmeyer flask equipped with a magnetic stirrer was placed 24 gm (84 mmol) of 3-(4'-chlorophenacyl)phthalide in 150 ml of 1,2-dichloroethane. While maintaining the solution between 55° and 60° C., 14.4 gm (90 mmol) of bromine in 40 ml of 1,2-dichloroethane was added dropwise during 15 minutes. Stirring was continued for another half hour and about 50 ml of 1,2-dichloroethane was added dropwise to the cooled solution. The organic layer was washed with dilute hydrochloric acid and concentrated. Recrystallization of the residue from chloroform/ethanol afforded 17 gm (72%) of a yellow solid, mp 174°–175° C., whose nmr was identical with the previously characterized sample of Example 6 before isomer separation.

EXAMPLE 8

3-(2',5'-dichlorophenacylidene)phthalide in 88% yield was prepared in accordance with the procedure described in Example 5, using 3-($\alpha$-bromo-2',5'-dichlorophenacyl)phthalide as the precursor. The purified product melted at 145°–147° C.

Analysis for $C_{16}H_8Cl_2O_3$: Calculated: C=60.22; H=2.53; Found: C=60.56; H=2.48.

EXAMPLE 9

3-(3',4'-dichlorophenacylidene)phthalide in 54% yield was prepared in accordance with the procedure described in Example 5, using 3-($\alpha$-bromo-3',4'-dichlorophenacyl)phthalide as the precursor. The purified product melted at 206°–209° C.

Analysis for $C_{16}H_8Cl_2O_3$: Calculated: C=60.22; H=2.53; Cl=22.22 Found: C=60.20; H=2.55; Cl=22.31

EXAMPLE 10

3-(1'-naphthoylmethylene)phthalide in 85% yield was prepared in accordance with the procedure described in Example 5 using 3-($\alpha$-bromo-1'-naphthoylmethyl)phthalide as the precursor. The purified product melted at 169°–171° C.

Analysis for $C_{20}H_{12}O_3$: Calculated: C=79.99; H=4.03 Found: C=79.83; H=3.77

EXAMPLE 11

3-(4'-fluorophenacylidene)phthalide in 40% yield was prepared in accordance with the procedure described in Example 5 using 3-($\alpha$-bromo-4'-fluorophenacyl)phthalide as the precursor. The purified product melted at 140°–141° C.

Analysis for $C_{16}H_9FO_3$: Calculated: C=71.64; H=3.38, Found: C×71.54; H=3.21

EXAMPLE 12

3-(3',5'-dimethoxyphenacylidene)phthalide in 51% yield was prepared in accordance with the procedure described in Example 5 using 3-($\alpha$-bromo-3,5-dimethoxyphenacyl)phthalide as the precursor. The purified product melted at 174°–175° C.

Analysis for $C_{18}H_{14}O_5$: Calculated: C=69.67; H=4.55; Found: C=69.46; H=4.58.

EXAMPLE 13

3-(2'-nitrophenacylidene)phthalide in 40.5% yield was prepared in accordance with the procedure described in Example 5 using 3-(α-bromo-2'-nitrophenacyl)phthalide as the precursor. The purified product melted at 180.5° C.

Analysis for $C_{16}H_9NO_5$: Calculated: C=65.09; H=3.07; N=4.74 Found: C=64.97; H=3.11; N=4.70

EXAMPLE 14

3-(4'-bromophenacylidene)phthalide in 40.5% yield was prepared in accordance with the procedure described in Example 5 using 3-(α-bromo-4'-bromophenacyl)phthalide as the precursor. The purified product melted at 220° C.

Analysis for $C_{16}H_9Br_1O_3$: Calculated: C=58.38; H=2.76 Found: C=58.23; H=2.76

EXAMPLE 15

3-(2'-methoxyphenacylidene)phthalide in 36% yield was prepared in accordance with the procedure described in Example 5 using 3-(α-bromo-2'-methoxyphenacyl)phthalide as the precursor. The purified product melted at 114° C.

Analysis for $C_{17}H_{12}O_4$: Calculated: C=72.85; H=4.32 Found: C=72.72; H=4.34

EXAMPLE 16

3-(2'-chlorophenacylidene)phthalide in 66% yield was prepared in accordance with the procedure described in Example 5 using 3-(α-bromo-2'-chlorophenacyl)phthalide as the precursor. The purified product melted at 98° C.

Analysis for $C_{16}H_9O_3Cl$: Calculated: C=67.50; H=3.19; Cl=12.45. Found: C=67.47; H=3.22; Cl=12.54.

EXAMPLE 17

3-(3',4'-dimethoxyphenacylidene)phthalide in 69% yield was prepared in accordance with the procedure described in Example 5 using 3-(α-bromo-3',4'-dimethoxyphenacyl)phthalide as the precursor. The purified product melted at 166° C.

Analysis for $C_{18}H_{14}O_5$: Calculated: C=69.67; H=4.55; Found: C=69.54; H=4.58.

EXAMPLE 18

3-(3'-methylphenacylidene)phthalide in 51% yield was prepared in accordance with the procedure described in Example 5 using 3-(α-bromo-3'-methylphenacyl)phthalide as the precursor. The purified product melted at 118°-119° C.

Analysis for $C_{17}H_{12}O_4$: Calculated: C=72.85; H=4.32; Found: C=72.82; H=4.33.

EXAMPLE 19

3-(2',5'-dimethoxyphenacylidene)phthalide in 34% yield was prepared in accordance with the procedure described in Example 5 using 3-(α-bromo-2',5'-dimethoxyphenacyl)phthalide as the precursor. The purified product melted at 136° C.

Analysis for $C_{18}H_{14}O_5$: Calculated: C=69.67; H=4.55; Found: C=69.51; H=4.54.

EXAMPLE 20

3-(3'-trifluoromethylphenacylidene)phthalide in 23.5% yield was prepared according to the procedure described in Example 5 using 3-(α-bromo-3'-trifluoromethylphenacyl)phthalide as the precursor. The purified product melted at 148°-149° C.

Analysis for $C_{17}H_9F_3O_3$: Calculated: C=64.16; H=2.85. Found: C=64.23; H=2.89.

EXAMPLE 21

3-(α-bromophenacylidene)phthalide was prepared according to the following procedure. A 500 ml flask was charged with 19 gm (75 mmol) of 3-phenacylphthalide in 200 ml of carbon tetrachloride and brought to reflux by means of a sunlamp. A solution of 32 gm (200 mmol) of bromine in 50 ml of carbon tetrachloride was added dropwise, and the refluxing was continued until the dibromination was completed to form 3-(α,α-dibromophenacyl)phthalide. The solution was then concentrated at atmospheric pressure to about 100 ml and cooled. A 20 ml portion of triethylamine was slowly added, and the flask was placed for one hour on a steambath and then cooled. The precipitated triethylamine salt was filtered off, and the organic phase was washed with diluted hydrochloric acid and dried over sodium sulfate. Petroleum ether was added to precipitate 16 gm (65%) of 3-(α-bromophenacylidene)phthalide, mp 138°-139° C.

Analysis for $C_{16}H_9BrO_3$: Calculated: C=58.38; H=2.76; Br=24.28. Found: C=58.47; H=2.82; Br=24.21.

EXAMPLE 22

4-methoxy-3-phenacylidenephthalide was prepared in 91% yield according to the procedure described in Example 5 using 4-methoxy-3-(α-bromophenacyl)phthalide as the precursor. The purified product had a melting point of 165° C.

Analysis for $C_{17}H_{12}O_4$: Calculated: C=71.83; H=4.26; Found: C=71.76; H=4.21.

EXAMPLE 23

4-chloro-3-phenacylidenephthalide was prepared in 27% yield according to the procedure described in Example 5 using 4-chloro-3-(α-bromophenacyl)phthalide as the precursor. The purified product had a melting point of 148° C.

Analysis for $C_{16}H_9ClO_3$: Calculated: C=67.50; H=3.19; Cl=12.45. Found: C=67.37; H=3.20; Cl=12.51.

EXAMPLE 24

4-methoxy-3-(2',5'-dimethoxyphenacylidene)-phthalide in 100% yield was prepared in accordance with the procedure described in Example 5 using 4-methoxy-3-(α-bromo-2',5'-dimethoxyphenacyl)phthalide as the precursor. The purified product has a melting point of 156° C.

Analysis for $C_{19}H_{16}O_6$: Calculated: C=67.05; H=4.74 Found: C=66.36; H=4.72

EXAMPLE 25

7-chloro-3-phenacylidenephthalide in 80% yield was prepared in accordance with the procedure described in Example 5 using 7-chloro-3-(α-bromophenacyl)phthalide as the precursor. The purified product had a melting point of 168°-170° C.

Analysis for $C_{16}H_9ClO_3$: Calculated: C=67.50; H=3.19; Cl=12.45. Found: C=67.43; H=3.19; Cl=12.46.

EXAMPLE 26

3-(4'-n-butoxyphenacylidene)phthalide was prepared in accordance with the procedure described in Example 5 using 3-(α-bromo-4'-n-butoxyphenacyl)phthalide as the precursor. The purified product, a mixture of the cis and trans isomers, had melting points of 80° and 96° C.

Analysis for $C_{20}H_{18}O_4$: Calculated: C=74.52; H=5.63 Found: C=74.50; H=5.67

EXAMPLE 27

3-(2',4'-dimethoxyphenacylidene)phthalide in 81% yield was prepared in accordance with the procedure described in Example 5 using 3-(α-bromo-2',4'-dimethoxyphenacyl)phthalide as the precursor. The purified product had a melting point of 195°-198° C.

Analysis for $C_{18}H_{14}O_5$: Calculated: C=69.67; H=4.55; Found: C=69.60; H=4.27.

EXAMPLE 28

A mixture of the cis and trans isomers of 3-phenacylidenephthalide in 53% yield was prepared in accordance with the procedure described in Example 5 using 3-(α-chlorophenacyl)phthalide as the precursor. The mixed isomer product had a melting point of 148° C., and mass-spectrographic analysis showed it to be the same as the product of Example 5 before isomer separation.

EXAMPLE 29

3-(3'-methoxyphenacylidene)phthalide in 51% yield was prepared according to the procedure described in Example 5 using 3-(α-bromo-3'-methoxyphenacyl)phthalide as the precursor. The purified product had a melting point of 118°-119° C.

Analysis for $C_{17}H_{12}O_4$: Calculated: C=72.85; H=4.32 C=72.82; H=4.33

EXAMPLE 30

3-(4'-n-butylphenacylidene)phthalide in 95% yield was prepared according to the procedure described in Example 5 using 3-(α-bromo-4'-n-butylphenacyl)phthalide as the precursor. The purified product had a melting point of 103.5°-104° C.

Analysis for $C_{20}H_{18}O_3$: Calculated: C=78.41; H=5.92. Found: C=78.24; H=5.95.

EXAMPLE 31

A mixture of 3 gm (8 mmol) of 3-(2',3',5',6'-tetrafluoro-4'-methoxyphenacyl)phthalide in 40 ml of glacial acetic acid was heated and stirred at 55°-60° C., and 3 gm of molecular bromine in 20 ml of glacial acetic acid was added dropwise. The colorless solution of the α-brominated starting material was thereafter added to 260 ml of ice cold water with vigorous stirring. The white precipitate was filtered and dried, dissolved in 150 ml of methylene chloride and refluxed for 2 hours in the presence of 3 ml of triethylamine. Dilute acid washing, followed by concentration and recrystallization from ethanol gave 1.1 gm (45%) of 3-(2',3',5',6'-tetrafluoro-4'-methoxyphenacylidene)phthalide, mp 199°-200° C.

Analysis for $C_{17}H_8F_4O_4$: Calculated: C=57.97; H=2.29. Found: C=57.86; H=2.28.

EXAMPLE 32

3-(2',5'-diethoxyphenacylidene)phthalide in 65% yield was prepared according to the procedure described in Example 31 using 3-(α-bromo2',5'-diethoxyphenacyl)-phthalide as the precursor. The purified product had a melting point of 122°-123° C.

Analysis for $C_{20}H_{18}O_5$: Calculated: C=71.00; H=5.36. Found: C=70.76; H=5.41.

While the invention has been described herein with regard to certain representative examples for the purpose of illustrating its practice, it is not to be construed as limited thereto. Those skilled in the art will readily recognize the variations and modifications which can be made without departing from the spirit and scope of the invention.

What is claimed is:

1. A method for inhibiting the male reproductive component of a corn plant which comprises applying to said corn plant before or during the early stages of reproductive differentiation an effective, non-lethal amount of a compound having the formula

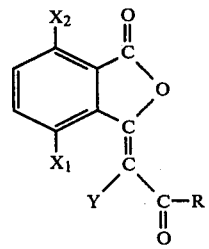

wherein R is selected from the group consisting of naphthyl, phenyl and substituted phenyl containing from 1 to 2 substituents selected from the class consisting of lower alkyl, lower alkoxy, halogen, trifluoromethyl and nitro; $X_1$ and $X_2$ are independently selected from the group consisting of hydrogen, halogen and lower alkoxy; and Y is selected from the group consisting of hydrogen, chlorine and bromine; provided that R is not 4-nitrophenyl and further provided that when $X_1$ is lower alkoxy, R is not 2,5-dimethoxyphenyl.

2. The method of claim 1 wherein $X_2$ is hydrogen.

3. A method according to claim 2 wherein $X_1$ is hydrogen.

4. A method according to claim 3 wherein the compound is 3-phenacylidenephthalide.

5. A method according to claim 3 wherein the compound is 3-(α-bromophenacylidene)phthalide.